United States Patent [19]
Linnebur et al.

[11] Patent Number: 4,997,428
[45] Date of Patent: Mar. 5, 1991

[54] DISPOSABLE DIAPER WITH LONGITUDINAL SUPERABSORBENT CONCENTRATION GRADIENT

[75] Inventors: Clemens Linnebur; Krzysztof Malowaniec, both of Heidenheim, Fed. Rep. of Germany

[73] Assignee: Paul Hartman Aktiengesellschaft, Heidenheim, Fed. Rep. of Germany

[21] Appl. No.: 263,634

[22] Filed: Oct. 27, 1988

[30] Foreign Application Priority Data

Oct. 27, 1987 [DE] Fed. Rep. of Germany ....... 3736275

[51] Int. Cl.5 .............................. A61F 13/15
[52] U.S. Cl. .................... 604/368; 604/374; 604/381
[58] Field of Search ............... 604/367–369, 604/374, 375, 378, 381

[56] References Cited

U.S. PATENT DOCUMENTS

| 3,604,422 | 9/1971 | Sabee | 128/287 |
| 3,779,246 | 12/1973 | Mesek et al | 128/287 |
| 3,799,167 | 3/1974 | Miller et al. | 128/287 |
| 3,945,386 | 3/1976 | Anczurowski et al. | 128/287 |
| 4,107,426 | 8/1978 | Gordon | 536/56 |
| 4,699,619 | 10/1987 | Bernardin | 604/378 |
| 4,699,823 | 10/1987 | Kellenberger et al. | 428/219 |
| 4,798,603 | 1/1989 | Meyer et al. | 604/378 |

FOREIGN PATENT DOCUMENTS

| 122042 | 10/1984 | European Pat. Off. . |
| 059015 | 8/1985 | European Pat. Off. . |
| 157649 | 10/1985 | European Pat. Off. . |
| 185593 | 6/1986 | European Pat. Off. . |
| 205674 | 12/1986 | European Pat. Off. . |
| 1914179 | 10/1979 | Fed. Rep. of Germany . |
| 3342963 | 6/1985 | Fed. Rep. of Germany . |

Primary Examiner—C. Fred Rosenbaum
Assistant Examiner—Adam J. Cermak
Attorney, Agent, or Firm—Dick and Harris

[57] ABSTRACT

A hygienic disposable article used as a diaper and possessing an absorbent body enhanced with expandable material. The expandable material is to be applied along the direction of the longitudinal axis of the diaper, in decreasing quantity outwards from the crotch area in such a way that the concentration of the expandable material in the crotch area is 8% to 40% of the weight of said absorbent body, while in the area of the waist, it is 1% to 7% thereof. In this way an optimal distribution of the absorbent components of the diaper is achieved in accordance with the distribution pattern of the fluid excreted from the wearer.

3 Claims, 2 Drawing Sheets

U.S. Patent  Mar. 5, 1991  Sheet 1 of 2  4,997,428
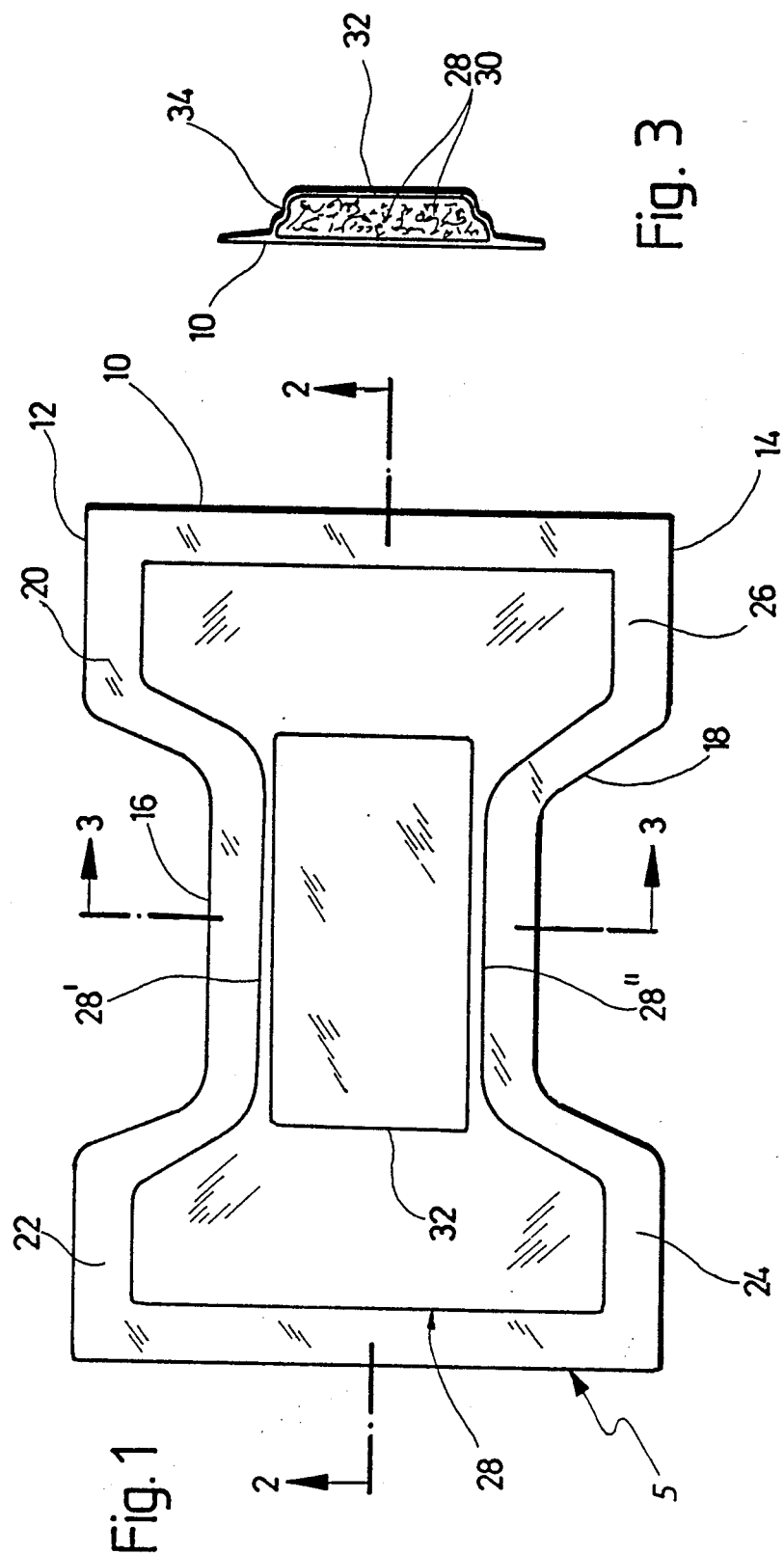

DISPOSABLE DIAPER WITH LONGITUDINAL SUPERABSORBENT CONCENTRATION GRADIENT

BACKGROUND OF THE INVENTION

The invention relates to a hygienic disposable article made from wood-pulp of the type configured for use as a diaper, having a linen-protecting sheet, a porous covering of non-woven material arranged to face the wearer's body, and an absorbent body arranged between the protecting sheet and the porous covering extending from the crotch area to the waist area, the absorbent body being composed of a mixture of wood-pulp fibers fibers and expandable materials, and further having a reinforcement area arranged in the crotch area, along the longitudinal axis of the diaper.

An absorbent body with expandable materials which are uniformly embedded in the absorbent body is already known from European Patent EP-A-O No. 157,649. As a result of the reinforcing of the center, it is true that a definite quantitative concentration is achieved in the crotch area; however, there does not ensue an optimal adaptation of these super-absorbent expandable materials to the actual distribution of the accumulating fluid. Likewise, such a uniform distribution of the expandable materials in the absorbent body has the disadvantage that in the end-areas of the diaper there are located large quantities of expandable materials which may not be effectively used; on the other hand, in manufacturing, they operate disadvantageously insofar as they cause blunting of the cutter blades. Also, in the end-areas of the diaper, those expandable materials that are present as granules escape from the diaper.

Especially suitable as expandable materials are polymers that form hydrogels, as they are described in European Patent EP-A-O No. 205,674. These are highly expandable polymers which expand slowly upon the entry of a fluid and which store up fluid in large volume.

The basic objective of the invention is to provide for an optimal distribution of the absorbent components of the diaper, corresponding in large measure to the distribution pattern of the fluid as it prevails in the diaper and presenting an optimal characteristic curve of fluid uptake. In this way, an economical use of the specified quantity of expandable materials is facilitated by concentrating them precisely where, in actual experience, the most copious fluid accumulation occurs in the diaper.

SUMMARY OF THE INVENTION

The objectives of the invention are attained in a manner whereby the expandable materials are applied in the direction of the longitudinal axis of the diaper with diminution outwards from the reinforcement region, in such a way that the concentration of the materials in the absorbent body is 8% to 40% of the weight of said absorbent body in said reinforcement area, whereas it is only 1% to 7% of the weight thereof in the area of the waist. In this way, it is also ensured that only a small amount of expandable materials is present in the end-areas of the diaper, with the result that the cutter blades are spared during the shearing of the product web into individual units.

In a preferred exemplification of the invention, the concentration of the expandable materials in the crotch area of the absorbent body is approximately 10% to 15%, whereas in the areas of the waist it is 2% to 5%.

A process for the manufacture of a hygienic disposable article according to the invention comprises the steps of continuously feeding a mixture of wood-pulp fibers via a first air current towards an air penetrable carrier and feeding expandable materials in intermittently increasing and decreasing quantitative concentration via a second air current directed into the first air current towards the simultaneous thorough mixing of said wood-pulp fibers and said expandable materials so as to position the maximum amounts of expandable in the reinforcement areas. The first and second air currents are then aspirated towards and onto the air penetrable carrier to cause simultaneous thickening accumulation of the intermixed wood-pulp fibers and expandable materials, forming a continuous web of absorbent bodies and reinforcement regions. The absorbent bodies are then joined, upon upper and lower sides, respectively, to said protecting sheet and said porous cover, the continuous web then being cross-cut into separate finished diaper articles. The expandable materials are carried by the second air current so as to position the maximum amounts in the reinforcement regions.

In an alternative embodiment of the invention, a third air current, bearing a mixture of wood-pulp fibers is directed into the first air current in order to form the reinforcement areas of the absorbent bodies. The thickly accumulated segments of the absorbent bodies which form the reinforcement regions are shaped, in an alternate preferred embodiment of the invention, prior to being joined with the protecting sheet and the porous covering.

BRIEF DESCRIPTION OF THE DRAWINGS

FIG. 1 is a top plan view of the disposable diaper article which has been spread out;

FIG. 2 is a longitudinal cross-sectional view of the disposable diaper article along line 2—2 of FIG. 1;

FIG. 3 is a transverse cross-sectional view of the disposable diaper article along line 3—3 of Fig.

DETAILED DESCRIPTION OF THE DRAWINGS

Figure 4:
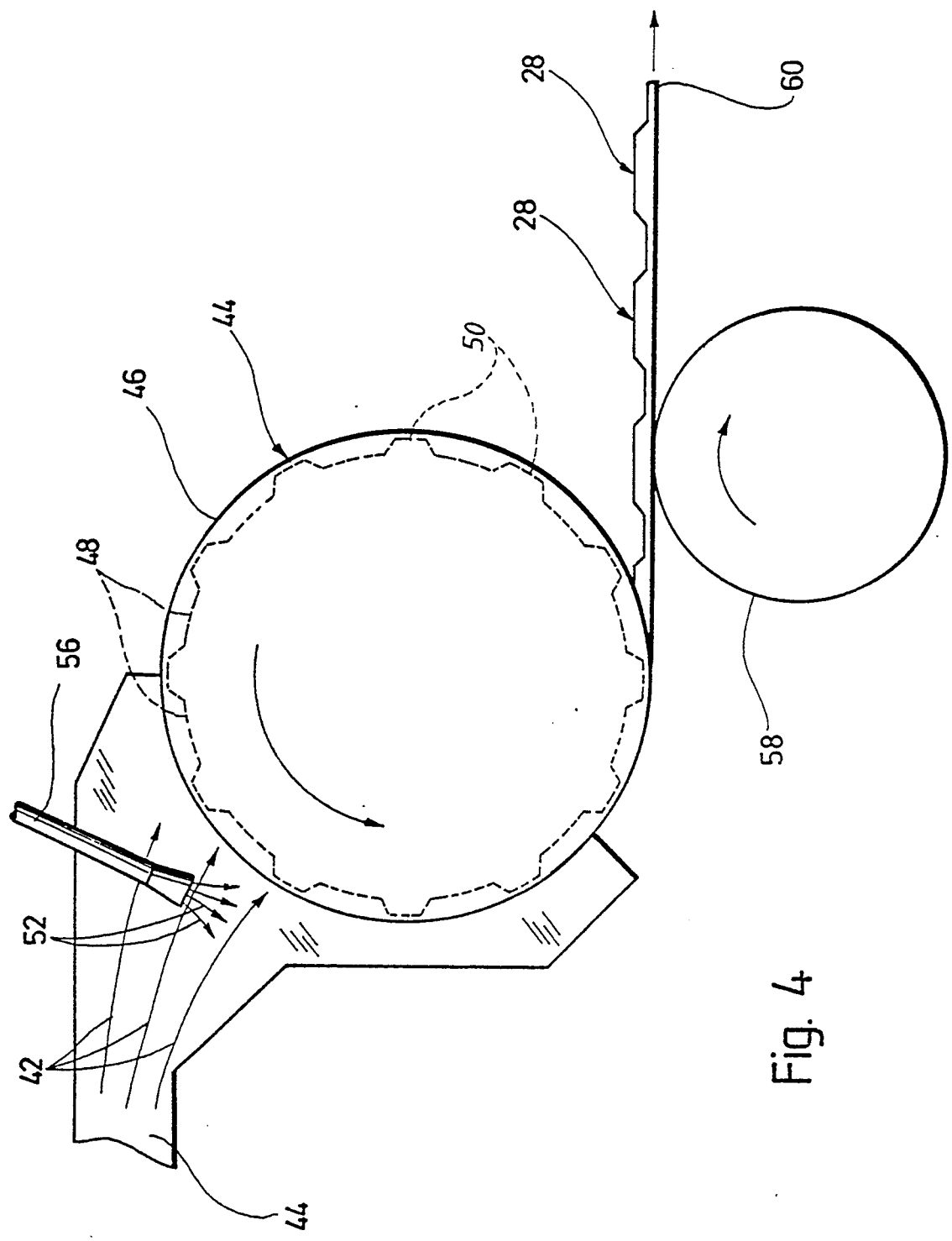
FIG. 4 is a schematic side elevational view of an apparatus for the implementation of the process.

While this invention is susceptible of embodiment in many different forms, there is shown in the drawings and will herein be described in detail, several specific embodiments, with the understanding that the present disclosure is to be considered as an exemplification of the principles of the invention and is not intended to limit the invention to the embodiments illustrated.

Disposable diaper article 5, according to the invention, as represented in FIG. 1, is provided with a linen-protecting sheet 10 which consists preferably of polyethylene. By way of example, this sheet is an essentially rectangular blank sheet which has cut-away leg-openings 16, 18 in the median area of both longitudinal borders 12 and 14 to define a crotch area. Sheet segments 20 and 22, and 24 and 26, lying to the side of cut-away leg-openings 16 and 18, respectively, surround a wearer's body in the area of the waist when the disposable diaper article 5 is put on.

Reference number 28 designates the entirety of an absorbent body which corresponds approximately to the outlines of the sheet blank in reduced dimensions. Absorbent body 28, in part, consists of a mixture of wood-pulp fibers 30. (FIG. 2) Absorbent body 28 is provided with a more densely applied, more effective fluid-absorbing reinforcement region 32, which is essentially rectangular and which, in the crotch area, is preferably terminated only a short distance from border 28', 28" of absorbent body 28 and which is homogeneous with the material of absorbent body 28 in the crotch area.

Absorbent body 28, including reinforcement region 32, is further blended with expandable materials, the concentration of which, commencing from reinforcement region 32 and proceeding in the direction of the longitudinal axis of the diaper, decreases towards the end areas of absorbent body 28. In the crotch area of absorbent body 28, in one preferred exemplification, the expandable materials represent approximately 10% to 15% by weight of the entire mass of the absorbent body and only 2% to 5% in its end areas. The weight of the wood-pulp fibers 30 per given unit of surface area is at least 20% greater in the crotch area than in the end-areas, that is to say in the waist area of the diaper, the result of which is an enhanced capacity for the absorption of body fluids in reinforcement region.

The absorbent body 28, together with reinforcement region 32 and linen-protecting sheet 10 are covered over their entire surface area by a porous sheet 34 of non-woven material which is intended for wearing against the flesh. If, for example, for reinforcement region 32 of absorbent body 28, one assumes a expandable material concentration of 12% and an absorbent-body weight of 600 grams per square meter, as well as a concentration of expandable materials of 3% for the remaining area of absorbent body 28 and a weight per unit surface area of 300 grams per square meter, then the ratio by volume of the expandable materials to fibrous material in the crotch area will be eight times that of the surrounding area. It is obvious that in this way, an optimal absorption capability of the diaper is obtained in precisely that area in which the most marked fluid accumulation occurs.

The device shown in FIG. 4 depicts a duct 40, which has arranged at one of its ends, drivable cylindrically shaped screen 44. Duct 40 partly encloses cylindrically shaped screen 44, which exhibits projecting rim parts 46 at its ends. Cylindrically shaped screen 44 is provided with recesses 48 along its circumference, which recesses 48 are separated from one another by means of broad fillets 50. Recesses 48 and fillets 50 serve to collect intermixed materials which are conveyed by first air current 42 and by second air current 52, and in the process of so doing, form individual absorbent bodies 28, or such bodies that are linked in continuous succession to one another.

Second air current 52, bearing expandable material, is introduced through pipe 56, which is roughly perpendicular to the direction of flow of first air current 42, and is conveyed into first air current 42, from which wood-pulp substances issue forth. Mixed first and second air currents 42 and 52 are drawn onto cylindrically shaped screen 44 by a vacuum source (not shown) which is connected to the interior of cylindrically shaped screen 44, whereby the entrained mixture of materials accumulates with increasing thickness at the periphery of cylindrically shaped screen 44.

The continuous web of material being formed in this way is taken tangentially off cylindrically shaped screen 44 and conducted onto a roller 58 by means of conveyer belt 60 of the subsequent processing stages (not shown), such as attachment of the linen-protecting sheet 10 and porous cover 34 of non-woven material, application of elastic bands and fastening devices, either before or after separation by cutting. After this, the continuous web thus completed is subdivided by transverse severing into individual articles.

By means of the second air current 52, the expandable materials are conveyed in intermittently increasing and decreasing quantitative concentrations to the first air current 42, in such a way that the maximum absorbency is achieved in the reinforcement region 32 of the absorbent bodies 28, the greatest portions of the intermittent air current bearing the expandable materials being directed, in each case, toward reinforcement region 32.

The foregoing description and drawings merely explain and illustrate the invention, and the invention is not limited thereto except insofar as the appended claims are so limited, as those skilled in the art who have the disclosure before them will be able to make modifications and variations therein without departing from the scope of the invention.

What is claimed is:

1. Hygienic disposable article, configured for use as a diaper and accordingly, of the type having:
   linen-protecting sheet means,
   porous covering means composed of non-woven material and arranged to face the wearer's body,
   absorbent body means arranged between said linen-protecting sheet means, and said porous covering means, said absorbent body means extending from a crotch area into a waist area of said article, said absorbent body means being composed of a mixture of wood-pulp fibers and expandable material, said absorbent body means having a reinforcement region extending along a longitudinally center of the diaper, said reinforcement region being arranged along said crotch area homogeneously with said absorbent body means, said hygienic disposable article comprising:
   said expandable material including particles of a superabsorbent material, such as water-insoluble, highly waterabsorbent hydrogel, arranged along the direction of the longitudinal axis of said diaper, and applied in continuously decreasing quantity outwards from the portions of said reinforcement region proximate the crotch area, in such a way that the concentration of said particles of superabsorbent material in said absorbent body means, in said reinforcement region is 8% to 40% of the weight of said absorbent body means, while in the area of the waist, the concentration of said particles of superabsorbent material is 1% to 7% of the weight of said absorbent body means.

2. The invention according to claim 1, wherein said concentration of the particles of superabsorbent material comprises in said crotch area of said absorbent body means, approximately 10% to 15% of the weight of said absorbent body means and in said area of the waist, 2% to 5% of the weight of said absorbent body means.

3. The invention according to claim 1, wherein the weight per unit area of the wood-pulp fibers is at least 20% greater in said crotch area of said disposable diaper article than in said waist area of said disposable diaper article.

* * * * *

UNITED STATES PATENT AND TRADEMARK OFFICE
CERTIFICATE OF CORRECTION

PATENT NO.  : 4,997,428

DATED       : March 5, 1991

INVENTOR(S) : Linnebur, et al.

It is certified that error appears in the above-identified patent and that said Letters Patent is hereby corrected as shown below:

Col. 4, Line 44    Delete "waterabsorbent" instead insert --water-absorbent--

Signed and Sealed this

Twenty-seventh Day of October, 1992

Attest:

DOUGLAS B. COMER

Attesting Officer      Acting Commissioner of Patents and Trademarks

UNITED STATES PATENT AND TRADEMARK OFFICE
CERTIFICATE OF CORRECTION

PATENT NO. : 4,997,428

DATED : March 5, 1991

INVENTOR(S) : Linnebur, et al.

It is certified that error appears in the above-identified patent and that said Letters Patent is hereby corrected as shown below:

Col. 1, Lines 14-15    Delete "fibers fibers" and instead insert --fibers--

Signed and Sealed this

First Day of December, 1992

Attest:

DOUGLAS B. COMER

Attesting Officer    Acting Commissioner of Patents and Trademarks